United States Patent [19]

Edwards

[11] 4,295,874

[45] Oct. 20, 1981

[54] N-ALKYL OR ARYL-N-(TRICHLOROVINYLTHIO)-HALOMETHANE SULFONAMIDES

[75] Inventor: Laroy H. Edwards, Napa, Calif.

[73] Assignee: Chevron Research, San Francisco, Calif.

[21] Appl. No.: 115,590

[22] Filed: Jan. 28, 1980

[51] Int. Cl.³ .................... A01N 33/00; A01N 59/02; C07C 143/74

[52] U.S. Cl. ........................................ 71/67; 564/96; 564/97; 71/66

[58] Field of Search ................. 564/96, 97, 95; 71/66, 71/67

[56] References Cited

U.S. PATENT DOCUMENTS

| | | | |
|---|---|---|---|
| 2,779,788 | 1/1957 | Gysin et al. | 564/97 |
| 2,779,941 | 1/1957 | Gysin et al. | 564/99 |
| 3,178,447 | 4/1965 | Kohn | 424/244 X |
| 3,574,767 | 4/1971 | Kohn | 260/608 |
| 3,678,017 | 7/1972 | Shelton et al. | 564/99 X |
| 3,703,500 | 11/1972 | Nast et al. | 564/99 X |
| 3,925,555 | 12/1975 | Okuda et al. | 424/321 |
| 4,068,000 | 1/1978 | Edwards | 564/96 X |
| 4,097,512 | 6/1978 | Lam et al. | 260/453 RW |
| 4,098,810 | 7/1978 | Thym et al. | 260/453 RW |

FOREIGN PATENT DOCUMENTS 857906  1/1961  United Kingdom ................. 564/96

*Primary Examiner*—John Doll
*Attorney, Agent, or Firm*—J. A. Buchanan, Jr.; T. G. DeJonghe; L. S. Squires

[57] ABSTRACT

N-trichlorovinylthio-substituted halomethanesulfonamides of the formula

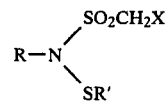

wherein R is alkyl, cycloalkyl, aryl, X is fluoro, chloro, bromo or iodo and R' is trichlorovinyl, are fungicides and algicides.

9 Claims, No Drawings

N-ALKYL OR ARYL-N-(TRICHLOROVINYLTHIO)-HALOMETHANE SULFONAMIDES

BACKGROUND OF THE INVENTION

U.S. Pat. No. 3,178,447, issued to G. K. Kohn on Apr. 13, 1965, discloses the fungicidal activity of N-polyhaloethylthio-substituted aryl- and alkanesulfonamides.

U.S. Pat. No. 2,779,788, issued to H. Gysin et al on Jan. 29, 1957, discloses fungicidal N-trichloromethylthio-substituted chloromethanesulfonamides.

U.S. Pat. No. 3,925,555, issued to I. Okuda et al on Dec. 9, 1975, discloses the control of mites with chloromethanesulfonamides.

U.S. Pat. No. 4,068,000, commonly assigned herewith, discloses mite ovicidal N-tetrachloroethylthio-substituted halomethanesulfonamides.

U.S. Pat. No. 3,574,767 discloses bis-(tetrahaloethyl)- and bis-(trihalovinyl)-trisulfides.

DESCRIPTION OF THE INVENTION

The fungicidal and algicidal compounds of the invention are represented by the formula

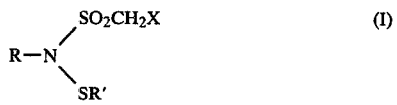

wherein R is alkyl of 1 to 8 carbon atoms, cycloalkyl of 5 to 8 carbon atoms substituted with up to 2 alkyl of 1 to 3 carbon atoms, phenyl substituted with up to 2 fluoro, chloro, bromo, iodo or alkyl of 1 to 4 carbon atoms; X is fluoro, chloro, bromo or iodo and R' is trichlorovinyl.

Representative R groups include alkyl such as methyl, ethyl, isopropyl, sec-butyl and hexyl; cycloalkyl and alkylcycloalkyl such as cyclopentyl, 2-methylcycloalkyl, 3-methylcyclohexyl, 3,5-dimethylcycloheptyl and cyclooctyl; and aryl groups such as phenyl, 2-fluorophenyl, 3-chlorophenyl, 4-bromophenyl, 4-iodophenyl, 4-methylphenyl and 2-chloro-4-methylphenyl.

Preferred R groups are alkyl, especially alkyl of 1 to 4 carbon atoms and cycloalkyl of 5 to 6 carbon atoms substituted with up to 1 alkyl of 1 to 3 carbon atoms. The preferred X groups are chloro or bromo.

Representative compounds of formula (I) include N-cyclopentyl-N-(trichlorovinylthio)-chloromethanesulfonamide, N-cycloheptyl-N-(trichlorovinylthio)-bromomethanesulfonamide, N-(2-fluorophenyl)-N-(trichlorovinylthio)-iodomethanesulfonamide, N-(4-chlorophenyl)-(trichlorovinylthio)-bromomethanesulfonamide, N-(3-iodophenyl)-N-(trichlorovinylthio)-iodomethanesulfonamide, N-cyclohexyl-N-(trichlorovinylthio)-bromomethanesulfonamide, N-phenyl-N-(trichlorovinylthio)-chloromethanesulfonamide, N-isopropyl-N-(trichlorovinylthio)-fluoromethanesulfonamide, and N-(2,4-dichlorophenyl)-N-(trichlorovinylthio)-chloromethanesulfonamide.

The compounds of the invention are prepared by sulfenylating a sulfonamide of the formula RNHSO$_2$CH$_2$X (II), wherein R and X have same significance as previously defined, with a 1,1,2,2-tetrachloroethyl sulfenyl halide. The sulfenylation reaction is conducted by reacting substantially equimolar quantities of the sulfonamide (II) and the sulfenyl halide in the liquid phase in the presence of a base. Suitable bases are organic amines with a pyridine compounds, e.g., pyridine or alpha picoline, and lower trialkylamines, e.g., triethylamine or tributylamine, and inorganic alkali metal hydroxides, e.g., sodium hydroxide or potassium hydroxide. Generally, at least one mol of base is employed for each mol of tetrachloroethyl sulfenyl halide. The exothermic reaction is normally conducted in an inert liquid diluent, e.g., organic solvents such as chlorinated hydrocarbons. The tetrachloroethyl group dehydrohalogenates in situ to form the trichlorovinyl group.

Preferably, the reaction is conducted in the presence of catalytic amounts of a quaternary ammonium salt. Generally, amounts of quaternary ammonium salt per mol of the sulfenyl halide reactant vary from about 0.01 to 0.3, although amounts from 0.05 to 0.2 mol per mol of the sulfenyl halide are preferred. Suitable quaternary ammonium salts are tetraalkylammonium halides wherein the alkyl has 1 to 6 carbon atoms and the halide is fluoro, chloro, bromo or iodo, e.g., tetramethaneammonium chloride or tetrabutylammonium bromide.

The sulfenylation reaction is conducted at a temperature of 0° C. to the boiling point of the diluent, although temperatures between 0° C. and 100° C. are preferred. The reaction is conducted at or above atmospheric pressure. The reaction time will, of course, vary depending on the reaction temperature and the particular reactants employed. Generally, the reaction is completed within one-half to 24 hours. The product (I) is isolated and purified by conventional procedures such as extraction, filtration, crystallization and chromatography.

The compounds of the invention have been found to be useful as fungicides and algicides.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus and the particular compound of the invention. As with most pesticidal compounds, the fungicides of the invention are not usually applied full strength, but are generally incorporated with conventional biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

The percentages by weight of the fungicide may vary according to the manner in which the composition is to be applied and the particular type of formulation, but in general comprise 0.5% to 95% of the toxicant by weight of the fungicidal composition.

The fungicidal compositions may be formulated and applied with other active ingredients, including other fungicides, insecticides, nematocides, bactericides, plant growth regulators, fertilizers, etc.

The compounds of the invention are also useful for controlling microbiological organisms such as algae and molds and occasionally aquatic weeds which foul aqueous industrial effluents and cooling streams, such as those occurring in the paper and food processing industries. They may also be used to control such organisms in other aqueous bodies such as lakes, streams, canals, pools and the like. When so used, a biocidal quantity of one or more of the compounds of this invention is added to the aqueous growth environment of the organisms. Usually, this dosage will range between about 0.1 to 50 ppm. In any given instance, the optimum dosage will depend upon the particular organism and aqueous body involved. For instance, when used to control algae, these compounds will usually be employed at concentrations of about 0.1 to 10 ppm. In terms of pounds of compound per acre of water one foot deep 0.1 to 10 ppm is equal to about 0.3 to 30 pounds per acre of water one foot deep. These compounds may be applied to the aqueous growth environments of such organisms as dispersible powders or in solution with water-miscible solvents.

EXAMPLE 1—Mycelial Inhibition

The compound of Example 3 of the present invention was evaluated for fungicidal effectiveness by means of a mycelial inhibition test. This test is designed to measure the fungitoxic activity of fungicidal chemicals in terms of their degree of inhibition of mycelium growth. The compound to be tested was dissolved in acetone to 500 ppm concentration. Paper strips were inoculated with the particular mycelium growth by dipping the paper into a potato dextrose both culture of mycelial suspension. The inoculated papers were then placed on potato dextrose agar plates and sprayed by means of a micro sprayer with the fungicidal solution. The treated paper strips were incubated at 25° C. and data is taken after 24 hours. Fungicidal activities are measured by a zone of inhibited mycelial growth from the center of the paper strip in terms of Mg/cm$^2$ needed for 99% control of the fungus (ED$_{99}$). The effectiveness of the compounds tested for fungicidal activity is reported in Table I in terms of the percent of the ED$_{99}$ of the test compound of the ED$_{99}$ of the standard Difolatan ®; except for *Botrytis cinerea* for which Phaltan ® was used as the standard.

EXAMPLE 2—Algae and Aquatic Plant Control

The compound of Example 3 was tested as an algicide and aquatic plant herbicide by the following method. The aquatic test species were Lemna, Elodea and Spirulina. An acetone solution of the test compound and a small amount of an alkylarylpolyoxyethylene glycol-containing surfactant was prepared. This solution was mixed with a nutrient solution in a quantity sufficient to give a concentration of 2 ppm. This mixture was put in clear 240 ml containers. A sample of the aquatic species was added to each container and the container was then placed in an illuminated environment and maintained at a temperature of about 20° C. for incubation. The containers were observed periodically for growth (as compared to an untreated check). The effectiveness of the test compound was determined based on a final observation of growth after 7 to 10 days. The results of the test on a 0 to 100 basis—0 indicating no effectiveness and 100 indicating complete effectiveness—are reported in Table II.

EXAMPLE 3—Preparation of N-isopropyl-N-(trichlorovinylthio)-chloromethanesulfonamide A 11.8 g (0.2 mol) sample of isopropylamine was added dropwise to a cooled (−60° C.) solution of 19.3 g (0.1 mol) chloromethanesulfonyl bromide in 200 ml dichloromethane. The reaction was then allowed to warm to about 25° C. and stirred about 16 hours. The reaction mixture was then filtered, washed with water, dried over magnesium sulfate and evaporated to give crude N-isopropyl chloromethanesulfonamide.

A 32.3 g (0.32 mol) sample of triethylamine was added dropwise to a cooled (0° C.) solution of 50 g (0.29 mol) N-isopropyl chloromethanesulfonamide and 70 g (0.29 mol) 1,1,2,2-tetrachloroethylsulfenyl chloride. After the addition was completed, the reaction was stirred at ambient temperature for 30 minutes and then under reflux for 3 hours. The reaction mixture was then cooled, washed with water, dried over magnesium sulfate and evaporated under reduced pressure to give the N-isopropyl-N-(trichlorovinylthio)-chloromethanesulfonamide product, which after crystallization from pet. ether melted at 71°–73° C. The product is reported as Compound 1.

Analysis S:Calc. 19.26; Fd. 19.6 Cl:Calc. 42.58; Fd. 40.5.

TABLE I

| Mycelia Inhibition |   |
| --- | --- |
| $\dfrac{\text{ED}_{99} \times 100}{\text{ED}_{99} \text{ (Standard)}}$ | |
| Compound 1 | |
| *Pythium ultimum* | 0 |
| *Rhizoctonia solari* | 91 |
| *Fusarium moniloforma* | 0 |
| *Botrytis cinera* | — |
| *Aspergillus niger* | 77 |

TABLE II

| Aquatic Weed and Algae Control, % | | | |
| --- | --- | --- | --- |
|  | Spirulina | Lemna | Elodea |
| Compound 1 | 0 | 60 | 90 |
| Reference compound* | — | 0 | 0 |

*N-isopropyl-N-(1,1,2,2-tetrachloroethyl)-chloromethanesulfonamide.

What is claimed is:

1. A compound of the formula

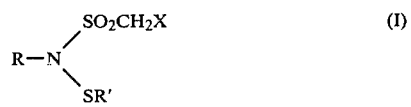

(I)

wherein R is alkyl of 1 to 8 carbon atoms, cycloalkyl of 5 to 8 carbon atoms substituted with up to 2 alkyl of 1 to 3 carbon atoms, or phenyl substituted with up to 2 fluoro, chloro, bromo, iodo or alkyl of 1 to 4 carbon atoms; X is fluoro, chloro, bromo or iodo and R' is trichlorovinyl.

2. A compound of claim 1 wherein R is alkyl of 1 to 4 carbon atoms.

3. The compound of claim 2 wherein X is chloro and R is isopropyl.

4. A method of controlling algae comprising contacting said algae or their growth environment with an algicidally effective amount of a compound of the formula defined in claim 1.

5. The method of claim 4 wherein X is chloro and R is isopropyl.

6. An algicidal composition comprising a biologically inert carrier and an algicidally effective amount of a compound of the formula defined in claim 1.

7. The composition of claim 6 wherein X is chloro and R is isopropyl.

8. A method of controlling aquatic plants comprising contacting said plants or their growth environment with an amount of a compound of the formula defined in claim 1 which is effective to kill or inhibit the growth of said plants.

9. The method of claim 8 wherein X is chloro and R is isopropyl.

* * * * *